United States Patent [19]

Stuart et al.

[11] Patent Number: 4,801,545
[45] Date of Patent: Jan. 31, 1989

[54] ENHANCED SOMATIC EMBRYOGENESIS USING MALTOSE

[75] Inventors: David A. Stuart; Steven G. Strickland; James W. Nichol, all of Davis, Calif.

[73] Assignee: Plant Genetics, Inc., Davis, Calif.

[21] Appl. No.: 565,116

[22] Filed: Dec. 23, 1983

Related U.S. Application Data

[63] Continuation-in-part of Ser. No. 496,186, May 19, 1983, abandoned.

[51] Int. Cl.[4] .......................... C12N 5/00; C12N 5/02
[52] U.S. Cl. ........................... 435/240.45; 435/240.49; 435/240.5; 435/240.54
[58] Field of Search .................. 435/240, 241, 240.45, 435/240.49, 240.5, 240.54

[56] References Cited

U.S. PATENT DOCUMENTS 4,326,034  4/1982  Peel et al. ........................... 435/241

OTHER PUBLICATIONS

Ammirato 1984 "Induction, Maintenance, and Manipulation of Development in Embrygenic Cell Suspension Cultures", in *Cell Culture and Somatic Cell Genetics of Plants* vol. 1 Academic Press pp. 139–141, 150–151.
Skirvin 1981 "Fruit Crops", in *Cloning Agricultural Plants Via In Vitro Techniques,* Conger(Ed.) CRC Press pp. 51–55.
Maretzki et al. 1974 "Utilization and Metabolism of Carbohydrates in Cell and Callus Cultures", in *Tissue Culture and Plant Science,* (Street, Ed) pp. 329–361.
Rangan 1984 "Culture of Ovanes", in *Cell Culture and Somatic Cell Genetics of Plants,* vol. 1, Vasil (Ed.) Academic Press pp. 221–226.
Conger 1981 "Agronomic Crops", in *Cloning Agricultural Plants Via In Vitro Techniques,* Conger (Ed) CRC Press pp. 172–176, 206–215, 117–118.
Verma et al. 1977 "Influence of Carbohydrates on Quantitative Aspects of Growth and Embryo Formation . . . ", *Plant Physiol,* v59 81–85.
Tisserat et al. 1979 "Somatic Embryogenesis in Angiosperms", *Horticultural Rev.,* v1 pp. 40–43.
Kochba et al. 1973 "Effect of Culture Media on Embryoid Formation from Ovular Callus . . .", *Z. Pflanzenzuchtg.,* v69 156–162.
Button, James, "The Effects of some Carbohydrates on the Growth and Organization of Citrus Ovular Callus", *Z. Pflanzenphysiol. Bd.,* 88:61–68 (1978).
M. L. Christianson, D. A. Warnick, and P. S. Carson, "A Morphogenetically Competent Soybean Suspension Culture," *Science* 222:632–634 (1983).
J. P. Ranch, L. Oglesby, and A. C. Zielinski. "Plant Regeneration from Embryo-Derived Tissue Cultures of Soybeans." In Vitro Cellular and Developmental Biology 21:653–658, (1985).
D. W. R. White. "Plant Regeneration from Longterm Suspension Cultures of White Clover." Planta 162:1–7 (1984).
K. Horvath Beach and R. R. Smith. "Plant Regeneration from Callus of Red and Crimson Clover." Plant Sci. Lett. 16:231–237 (1979).
W. R. Scowcroft and J. A. Adamson. "Organogenesis from Callus Cultures of the Legume, *Stylosanthes hamata,*" Plant Sci. Lett. 7:39–42 (1976).
H. J. Jacobsen and W. Kysely. "Introduction of Somatic Embryos in Pea, *Pisum Sativum L.,*" Plant Cell Tissue and Organ Culture, 320–324 (1984).

*Primary Examiner*—Charles F. Warren
*Assistant Examiner*—David T. Fox
*Attorney, Agent, or Firm*—Limbach, Limbach & Sutton

[57] ABSTRACT

Methods and compositions are provided for the growth of cultured plant cells which include the addition of maltose as a carbohydrate source. Additional improvements in the plant cell growth medium can be obtained by adding a source of ammonium ion to the medium to obtain a synergistic effect with the maltose.

9 Claims, 1 Drawing Sheet

Round

Ellipsoid

Bottle

Round

Ellipsoid

Bottle

|⎣_____⎦ 5mm

ENHANCED SOMATIC EMBRYOGENESIS USING MALTOSE

RELATED APPLICATION DATA

This application is a continuation-in-part of application Ser. No. 496,186 filed May 19, 1983 now abandoned.

DESCRIPTION

1. Technical Field

This invention relates to the culturing of embryonic plant tissue and more specifically to improving the quantity and quality of embryos generated from somatic tissues when cultured on medium supplemented with selected carbon sources.

2. Background Art

The practice of plant breeding seeks to introduce systematic genetic changes into the plant species by a number of means. The source of new genetic material may come from the recombination of genes within a variety, species or closely related species using well known methods of plant breeding (Allard, R. W., *Principles of Plant Breeding,* John Wiley & Sons, New York, 1960; Simmons, N. W., *Principles of Crop Improvement,* Langman Group Ltd., London, 1979) to develop a new and more advantageous plant variety. Alternatively, distantly related species can be sexually crossed and the resulting embryo is cultured into a whole and fertile plant. Genetic recombination in plants can be accomplished by direct fusion of naked cells or cell parts to form a new variety. Other methods are being developed in which specific foreign genes of extremely diverse organisms can be combined in the plant. All of these methods can be loosely defined under the terms of plant breeding or genetic engineering.

The plant breeder also makes use of plant cloning at various stages in the development of new varieties. Cloning is performed to preserve or increase the number of individual plants without genetic recombination. For example, the breeder may wish to retain a single individual with an advantageous genetic compliment. Letting such an individual go to seed would result in recombination of those genes and loss of some of its characters. At other times breeders wish to preserve or increase parents of a hybrid. In other instances the breeder may wish to increase the numbers of individuals of a certain cross which posses hybrid character. Regardless of the need, the breeder seeks to use cloning as a way of increasing plant numbers and preventing genetic recombination.

Many methods for cloning of plants exist; somatic embryogenesis is one method. Certain advantages favor somatic embryogenesis for plant cloning. The process often begins by tissue culturing cells from a plant which has a known desirable phenotype. Cells are then subcultured for a number of generations. The generation of somatic embryos from callus tissue can be highly efficient, deriving from 10,000 to 100,000 individual embryos from one gram of starting cells. Regeneration can also be accomplished by fermenting embryos in a batch process. The advantages of this method may permit the production of genetically uniform embryos with the cost equal to field grown seed.

The tissue culturist seeks to produce numerous somatic embryos which are of high quality and able to grow into an entire plant possessing a root and shoot.

The process of producing embryos from somatic tissues generally employs a tissue culture medium which contains mineral salts, vitamins, plant hormones and a carbohydrate source. Generally sucrose is the recommended carbohydrate source for somatic embryogenesis to occur (Tisserat, B. et al. "Somatic Embryogenesis in Angiosperms", Horticultural Reviews 1:1-78 (1979)). Depending upon the species the sucrose concentration is generally between one and 18% (weight to volume) in the medium. Of six carbohydrates tested in eggplant somatic embryogenesis, sucrose was found to be the superior source (Gleddie, S. et al., "Somatic Embryogenesis and Plant Regeneration from Leafexplants and Cell Suspensions of *Solanum melongena* (eggplant)", Can. Journal Botany 61:656 (1983)). Glucose has been used in place of sucrose in carrot embryogenesis (Homes, J. L. A., "Influence de la concentration en glucose sur la development et al differentiation d'embryons formes dans des tissus de carotte cultives in vitro", C.N.R.S., p. 49-60, 1967, Strasburg. Les cultures de tisus de plantes, Coloq. Nat. C.N.R.S. Paris). Glucose, however, was found to be no better than sucrose in later studies using carrot cultures. (Verma, D. A. and D. K. Dougall, "Influence of Carbohydrates on Quantitative Aspects of Growth and Embryo Formation in Wild Carrot Suspension Cultures", Plant Physiol. 59:81 (1979)). Galactose has been reported to cause an increase in citrus embryo formation, as do the galactose containing sugars lactose and raffinose (Kochba, J. et al., In: Production of Natural Compounds by Cell Culture Methods (Ed. E. W. Alferman and E. Reinhard), GSF Munchen GDR pp. 223-232 (1978)).

Complex mixtures of carbohydrates such as malt extract (at up to 0.1% w/v) have been used frequently as a supplement to sucrose in the medium to improve somatic embryogenesis in citrus cultures (See Kochba, J. and P. Speigel-Roy, "Effect of Culture Media on Embryoid Formation from Ovular Callus of 'Shamonti' Orange (*Citrus sinensis*)", Zeit. Pflanzenzuchtg 69, 156, 1973, for latest reference on malt extract). No studies have been done to determine the active principle in malt extract.

Maltose has been used in several studies of plant tissue culture growth and differentiation without success. Mitra, G. C. and H. C. Chaturvedi, "Embryoids and Complete Plants from Unpollinated Ovaries and from Ovules of in vivo-grown Emasculated Flower Buds of Citrus spp", Bulletin Torrey Bot. Club 99:184, (1972) reported that maltose was not an effective additive for culturing zygotic embryos of citrus. Chong, C. and C. D. Taper, "Mallus Tissue Cultures. II. Soribitol Metabolism and Carbon Nutrition", Can. J. Bot. 52:2361, (1974) reported that apple cell cultures were inhibited from growth if maltose was included in the medium. Nash, D. T. and W. G. Bell, "Carbohydrate Nutrition of Paul's Scarlet Rose Cell Suspension", Can. J. Bot. 53:179, (1975) reported that maltose was also a very poor carbohydrate for cell growth. Using carrot cell cultures Verma and Dougall (supra) surveyed a large number of carbohydrates for their effect on growth and somatic embryo development. They concluded that growth and embryogenesis on a variety of sugars is correlated. They also concluded that sugars must be metabolized through common intermediates. They did not distinguish maltose as being superior to any other carbohydrate tested.

DISCLOSURE OF THE INVENTION

It is an object of this invention to provide methods and materials to increase the quantity and quality of somatic embryos produced from plant tissue.

It is further an object of this invention to provide optimized sources of carbohydrates for somatic embryogenesis.

It is yet another object of this invention to provide methods and materials allowing mass propagation of numerous species of plants through somatic embryogenesis.

It is a still further object of this invention to provide methods and materials for regeneration of numerous viable somatic embryos with identical genetic and phenotypic traits.

The present invention provides a medium for growing cultured plant cells comprising 7.5 to 300 mM maltose together with a balanced salt solution containing the plant cells nutrition and growth requirements.

Another aspect of the invention provides methods for culturing plant cells utilizing the media of this invention.

BRIEF DESCRIPTION OF THE DRAWING

The sole FIGURE is a graphic representation of various embryo morphologies produced in accordance with the present invention. The embryo morphologies are grouped as indicated, and described hereinafter in the specification.

BEST MODE FOR CARRYING OUT INVENTION

Figure 1:
Figure 1:
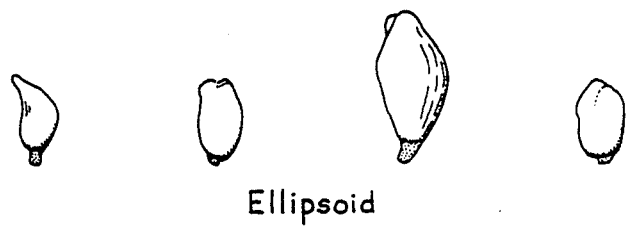
Figure 1:
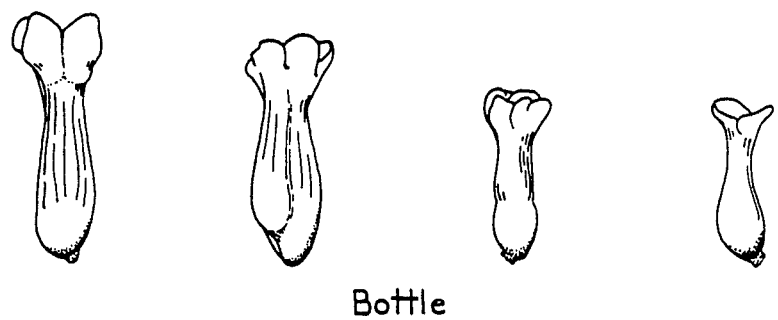

This invention provides methods and materials for enhancing the quality and quantity of somatic embryos produced from plant tissue derived from species which are capable of somatic embryogenesis.

Numerous important crop and horticultural species have been shown to be capable of propagation through tissue culture and somatic embryogenesis. These varieties include, but are not limited to:

TABLE 1

| Vegetable crops | Fruit and nut trees |
|---|---|
| alfalfa | almond |
| asparagus | apple |
| beet | banana |
| brussels sprouts | coffee |
| carrot | date |
| cauliflower | grapefruit |
| eggplant | lemon |
| onion | olive |
| spinach | orange |
| sweet potato | peach |
| tomato | Bulbs |
| Fruit and berries | lily |
| blackberry | daylily |
| grape | Easter lily |
| pineapple | hyacinth |
| strawberry | Flowers |
| Foilage | African violet |
| silver vase | anthruium |
| begonia | chrysanthemum |
| crytanthus | gerbera daisy |
| dieffenbachia | gloxinia |
| dracaena | petunia |
| eiddleleaf | rose |
| pointsettia | orchid |
| weeping fig | Pharmaceutical |
| rubber plant | atropa |
| Ferns | ginseng |
| Australia tree fern | pyrethium |
| Boston fern | Silviculture (forestry) |

TABLE 1-continued

| | |
|---|---|
| Maidenhair fern | douglas fir |
| rabbitsfoot fern | pine |
| staghorn fern | quaking aspen |
| sword fern | redwood |
| Cereal Grains | rubber tree |
| barley | |
| corn | |
| millet | |
| pennisetum | |
| wheat | |

For a more exhaustive list of species capable of somatic embryogenesis, see Evans, D. A. et al., "Growth and Behavior of Cell Cultures: Embryogenesis and Organogenesis" in Plant Tissue Culture: Methods and Applications in Agriculture, Thorpe, ed., Academic Press, page 45 et. seq. (1981).

Cell Culture Media

The general requirements of tissue cultured plant cells for nutrition and growth have been determined by analysis of plant tissue. For example, Shenk-Hildebrandt (SH) culture medium was formulated in an attempt to recreate the normal environment of a plant cell (Shenk, R. V. and A. C. Hildebrandt, Can. J. Bot., 50:199-204 (1972)). Other known media for plant cell growth include, e.g. Murashige-Skoog (M-S) basal media (Murashige, T. and F. Skoog, Physiol. Plant., 15:473-97 (1962)) and White's (White, P. R., The Cultivation of Animal and Plant Cells, 2nd ed. Ronald Press Co., New York (1963)). A comprehensive list of plant cell media is contained in Huang, L. and T. Murashige, Plant Tissue Culture Media, TCA Manual 3:539-48, Tissue Culture Association, Rockville, M.D. (1977).

Overall, the substances required in common for plant cells nutrition and growth can be categorized as:

1. Salts of balanced pH and osmolarity.
2. Carbohydrates as carbon and energy sources.
3. Hormones and vitamins to mediate cell growth and development.

The previously mentioned media can be used, with some modification, for maintenance of the cultured cells as callus, as well as for induction of embryo formation and subsequent growth and development.

Carbohydrates

Sucrose is generally chosen as the carbohydrate source, for plant cell culture media; it is extremely abundant in the plant kingdom. Sucrose is a disaccharide ($\alpha$-D-glucopyranosyl-$\beta$-D-fructofuranoside) of glucose and fructose with a molecular weight of 342 daltons.

Maltose (4-D-$\alpha$-D-glucopyranosyl-$\beta$-D-glucopyranose) is also a common disaccharide of molecular weight 342 daltons, but consists of $\alpha[1-4]$ linked glucose residues. It can be obtained as a component of crude malt extract, but is widely available in purified form.

Although the maltose concentrations disclosed with this invention are indicated as either weight/volume percentages or molar solutions, it is understood that a 3% solution of maltose is approximately 88 mM.

Ammonium Ion and Reduced Nitrogen

A requirement for a source of reduced nitrogen for the formation of in vitro somatic embryos has been recognized in carrot cell cultures. This effect has since been confirmed and extended to a variety of other species. A detailed study of this reduced nitrogen requirement may be found in Walker, K. A. and S. J. Sato "Morphogenesis in Callus Tissue of *Medicago sativa:*

"The Role of Ammonium Ion in Somatic Embryo Genesis," Plant Cell Tissue Organ Culture, 1:109-21.

It has been found that various amino acids, individuallly and in combination, can supplement or substitute for ammonium ion as a source of reduced nitrogen. These amino acids include, e.g.: L-proline, L-alanine, L-glutamine and L-arginine, and their amides, alkyl esters and dipeptidyl derivatives.

Synergistic improvements are obtained in the quality and quantity of somatic embryos by using sources of reduced nitrogen together with maltose in various embodiments of the present invention.

Experimental

In alfalfa, embryogenesis can be routinely induced in the Regen S line of Saunders and Bingham, "Production of Alfalfa Plants from Callus Tissue, " Crop Sci. 12:804-808 (1972).

Plants of Medicago sativa cultivar Regen S derived from the cross of the varieties Vernal and Saranac were used. Callus was initiated by surface sterilizing petioles with 50% Clorox® for five minutes, washing with $H_2O$ and plating on Shenk-Hildebrandt medium (SH), Shenk, R. V. and A. C. Hildebrandt, Can. J. Bot., 50:199-204 (1972). The medium contained 25 μM, 2,4-dichlorophenoxyacetic acid (2,4-D) and 10 μM kinetin (termed maintenance medium). Callus which was formed on the explant tissue was separated from the remaining uncallused tissue and repeatedly subcultured on maintenance medium. Callus was subcultured at 3 week intervals and grown under indirect light at 27° C.

Three to nine grams of callus was collected at 17 to 24 days postsubculture from plates of maintenance medium and transferred to 100 ml of liquid SH containing 50 μM 2,4-dichlorophenoxyacetic acid (2,4-D) and 5 μM kinetin for induction. Walker, K. A., M. L. Wendeln and E. G. Jaworski, Plant Sci. Lett 16:23-30 (1979). Cells were cultured in 500 ml flasks for 3 days at 27° C. on an orbital shaker at 100 R.P.M. under indirect light.

Induced cells were aseptically sized by passing the cells through a series of stainless steel wire mesh sieves (Fisher Scientific) under a gentle vacuum. Cell clumps either fell or were forced through a 20 mesh (820 μM) and collected on a 60 mesh (230 μM) screen. Cells retained on the 60 mesh screen were washed with 500 ml of SH minus hormone medium for every 100 ml of induction culture volume. The washing medium was removed by vacuum. The fresh weight of the cell clumps was taken and cells were resuspended in SH medium without hormones at 150 mg fresh weight per ml. Seventy-five mg (0.5 ml) of resuspended cells were pipeted onto approximately 10 ml of agar solidified medium in 60 mm×15 mm petri dishes.

Alternatively, somatic embryogenesis in suspension culture will occur if 300 mg (2 ml) of resuspended cells are delivered to 8 ml of liquid SH medium contained in a 50 ml erlenmeyer flask. The embryogenesis medium contained SH medium ($NH_4^+$ equal to 2.6 mM) with 3% (w/v/) sucrose without hormones. Ammonium ion free medium was made by substituting an equivalent amount of $NaH_2PO_4$ for the $NH_4H_2PO_4$ of SH. The 25 mM $NH_4^+$ control medium consisted of ammonium free medium supplemented with 12.5 mM $(NH_4)_2SO_4$. All carbohydrate and amino acid sources were sterilized by 0.2 μm filtration and subsequently added to freshly autoclaved medium.

Each treatment was generally plated in 10 replicates. Dishes were Parafilm® wrapped and incubated for 21 days. Suspension flasks were foam plugged, sealed with Saran Wrap® and incubated for 14 days on an orbital shaker at 100 R.P.M. Incubation was at 27° C. under 12 hour illumination from cool white fluorescent tubes at 28 cm from solidified cultures or 2 m from suspension cultures.

Embryogenesis was visually measured after incubation by counting green centers of organization on the callus using a stereo microscope at magnification of 10×. Embryo size was measured using a calibrated ocular scale at 10× magnification. Embryo shape was determined by visual examination. Conversion of embryos to whole plants with root and shoot axis (first primary leaf) was done by aseptically transferring embryos at 21 days of initial culture to half-strength SH medium solidified with 0.8% agar.

EXAMPLE 1

Table 2 presents the results of an experiment in which induced alfalfa cells were regenerated in the presence of SH plus 25 mM $NH_4^+$ with a variety of carbohydrates. Maltose treatment resulted in not only the highest number of embryos but embryos which were larger and more highly developed than any other treatment. Embryo size has been used as one indicator of embryo quality.

TABLE 2

The effect of carbohydrate sources on alfalfa somatic embryogenesis.

| Chemical | (%; w/v) | Number of Embryos as % of Sucrose |
|---|---|---|
| sucrose | (3%) | 100 |
| maltose | (1%) | 108 |
|  | (3%) | 182 |
| malt extract | (1%) | 81 |
|  | (3%) | 189 |
| soluble starch | (1%) | 32 |
|  | (3%) | 36 |
| maltotriose | (1%) | 0 |
|  | (3%) | 1 |
| amylose | (1%) | 0 |
|  | (3%) | 0 |
| fructose | (1%) | 101 |
|  | (3%) | 117 |
| glucose | (1%) | 59 |
|  | (3%) | 80 |
| mannose | (1%) | 0 |
|  | (3%) | 0 |
| galactose | (1%) | 0 |
|  | (3%) | 0 |
| glucosamine | (1%) | 0 |
|  | (3%) | 0 |
| galactosamine | (1%) | 0 |
|  | (3%) | 0 |
| fucose | (1%) | 0 |
|  | (3%) | 0 |
| L-arabinose | (1%) | 0 |
|  | (3%) | 0 |
| D-arabinose | (1%) | 0 |
|  | (3%) | 0 |
| glucoheptose | (1%) | 0 |
|  | (3%) | 0 |
| mannoheptose | (1%) | 0 |
|  | (3%) | 0 |
| glucose-1-phosphate | (1%) | 0 |
|  | (3%) | 0 |
| glucose-6-phosphate | (1%) | 2 |
|  | (3%) | 0 |
| xylose | (1%) | 0 |
|  | (3%) | 0 |
| ribose | (1%) | 0 |
|  | (3%) | 0 |
| deoxyribose | (1%) | 0 |
|  | (3%) | 0 |
| rhamnose | (1%) | 0 |

TABLE 2-continued

The effect of carbohydrate sources on alfalfa somatic embryogenesis.

| Chemical | (%; w/v) | Number of Embryos as % of Sucrose |
|---|---|---|
|  | (3%) | 0 |
| erythrose | (1%) | 0 |
| lactose | (1%) | 0 |
|  | (3%) | 0 |
| celloboise | (1%) | 0 |
|  | (3%) | 0 |
| raffinose | (1%) | 44 |
|  | (3%) | 84 |
| stachyose | (1%) | 7 |
|  | (3%) | 47 |
| gentiobiose | (1%) | 36 |
|  | (3%) | 25 |
| melibiose | (1%) | 3 |
|  | (3%) | 1 |
| melezitose | (1%) | 0 |
|  | (3%) | 5 |

EXAMPLE 2

In Table 3 is shown the effect of maltose concentration on embryo numbers formed during alfalfa embryogenesis. At 15 mM and below few embryos are formed. Above 15 mM and up to 300 mM maltose caused the best embryo formation with 90 mM (about 3% w/v) being near the optimum concentration.

TABLE 3

The Effect of Adding Increasing Levels of Maltose to Cells Undergoing Somatic Embryogenesis

| Maltose Conc. (mM) | Somatic Embryo Number |
|---|---|
| 0 | 0 ± 0 |
| 7.5 | 85 ± 19 |
| 15 | 155 ± 15 |
| 30 | 209 ± 10 |
| 60 | 205 ± 19 |
| 90 | 259 ± 25 |
| 120 | 233 ± 32 |
| 180 | 234 ± 18 |
| 240 | 208 ± 23 |
| 300 | 159 ± 27 |

EXAMPLE 3

A variety of sources of maltose have been used and the results of these experiments are shown in Table 4. It is apparent that maltose is effective regardless of the source of the chemical.

TABLE 4

Carbohydrate source and embryogenesis in alfalfa tissue cultures. Cultures regenerated on SH plus 25 mM NH4+ plus carbohydrate at 3% (w/v).

| Carbohydrate | Source | Lot No. | Somatic Embryos |
|---|---|---|---|
| sucrose | Mallinckordt Chem. Co. | KTHG | 12 ± 3 |
| maltose | Calbiochem Behring Co. | 903236 | 126 ± 6 |
| maltose | Sigma Chem. Co. | 102F-0307 | 101 ± 8 |
| maltose | Sigma Chem. Co. | 121F-0224 | 115 ± 6 |

EXAMPLE 4

The effect of maltose on embryogenesis can be supplemented by added ammonium ion as shown in Table 5.

TABLE 5

Interaction of Maltose versus $NH_4^+$ for Regeneration of Somatic Embryos of Alfalfa.

| Maltose Conc. (%; w/v) | $NH_4^+$ Conc(mM) | Somatic Embryo Number |
|---|---|---|
| 3% | 0 | 0.2 ± 0.2 |
| 3 | 2.6 | 84.4 ± 9.8 |
| 3 | 7.5 | 188.5 ± 12.3 |
| 3 | 15 | 207.7 ± 14.2 |
| 3 | 30 | 159.9 ± 11.8 |
| 3 | 50 | 76.3 ± 7.6 |
| 3 | 75 | 63.4 ± 9.0 |
| 3 | 100 | 63.6 ± 9.0 |
| 6% | 7.5 | 189.3 ± 13.4 |
| 6% | 30 | 158.4 ± 17.9 |
| 6% | 50 | 78.1 ± 13.4 |
| 9% | 7.5 | 150.3 ± 9.9 |
| 9% | 30 | 121.3 ± 19.0 |
| 9% | 50 | 89.7 ± 7.5 |

The maltose effect is, therefore, enhanced by an interaction with ammonium ion and ammonium ion concentration can be optimized with respect to the maltose concentration to provide a synergistic effect.

EXAMPLE 5

Addition of maltose to sucrose containing medium is summarized in Table 6. Maltose has, by far, a lower threshold for stimulation of embryogenesis (Compare 0% maltose column versus 0% sucrose row) than sucrose. In this experiment, in which a limited range of carbohydrate concentrations were used, it is evident that 3% maltose plus 1% of sucrose yielded the highest embryo numbers. Overall, however embryogenesis is affected more by the presence of maltose than by sucrose.

TABLE 6

Interaction of Sucrose and Maltose for Somatic Embryogenesis in Alfalfa using SH + 25 mM $NH_4^+$

| % Sucrose (w/v) | % Maltose (w/v) | | | |
|---|---|---|---|---|
|  | 0 | 1 | 2 | 3 |
| 0 | 0 ± 0 | 240.2 ± 13.6 | 300.2 ± 26.4 | 326.6 ± 15.3 |
| 1 | 115.6 ± 11.8 | 268.0 ± 15.0 | 244.8 ± 17.5 | 284.0 ± 17.3 |
| 2 | 121.3 ± 8.2 | 250.2 ± 10.2 | 331.8 ± 25.8 | 316.2 ± 21.3 |
| 3 | 174.4 ± 9.6 | 298.9 ± 20.3 | 320.8 ± 16.4 | 298.0 ± 24.8 |

EXAMPLE 6

In Table 7 is shown the effect of regenerating embryos treated with various levels of $NH_4^+$, proline and maltose. A four-fold enhancement of embryogenesis is seen when the medium contains maltose and proline.

TABLE 7

Interaction of Carbohydrate $NH_4^+$ and Proline on Somatic Embryogenesis in Alfalfa.

| Carbohydrate | $NH_4^+$ (mM) | Proline (mM) | Somatic Embryo Number |
|---|---|---|---|
| 90 mM sucrose | 0 | 0 | 0.9 ± 0.3 |
| 90 mM sucrose | 2.6 | 0 | 42.9 ± 3.5 |
| 90 mM sucrose | 25 | 0 | 102.9 ± 9.3 |
| 90 mM sucrose | 0 | 100 | 93.2 ± 19.6 |
| 90 mM sucrose | 2.6 | 100 | 478.8 ± 37.0 |
| 90 mM sucrose | 25 | 100 | 535.1 ± 25.4 |
| 90 mM maltose | 0 | 0 | 0.7 ± 0.4 |
| 90 mM maltose | 2.6 | 0 | 88.8 ± 8.6 |

TABLE 7-continued

Interaction of Carbohydrate NH$_4^+$ and Proline on Somatic Embryogenesis in Alfalfa.

| Carbohydrate | NH$_4^+$ (mM) | Proline (mM) | Somatic Embryo Number |
|---|---|---|---|
| 90 mM maltose | 25 | 0 | 393.3 ± 25.2 |
| 90 mM maltose | 0 | 30 | 100.9 ± 17.8 |
| 90 mM maltose | 2.6 | 30 | 319.1 ± 17.4 |
| 90 mM maltose | 25 | 30 | 471.7 ± 34.8 |
| 90 mM maltose | 0 | 100 | 125.5 ± 17.9 |
| 90 mM maltose | 2.6 | 100 | 399.3 ± 40.8 |
| 90 mM maltose | 25 | 100 | 726.1 ± 22.3 |

EXAMPLE 7

The interactions observed in Example 6 can be shown with other amino acids. Table 8 presents the effect of various concentrations of NH$_4^+$, maltose and alanine or glutamine.

TABLE 8

Interaction of Carbohydrate, NH$_4$+ and Alanine or Glutamine on Somatic Embryogenesis in Alfalfa

| Carbohydrate | NH$_4^+$ (mM) | | Somatic Embryo Number |
|---|---|---|---|
| | | Alanine (mM) | |
| 90 mM sucrose | 0 | 0 | 0.7 ± 0.3 |
| 90 mM sucrose | 2.6 | 0 | 35.8 ± 3.8 |
| 90 mM sucrose | 0 | 30 | 14.0 ± 4.0 |
| 90 mM sucrose | 2.6 | 30 | 70.3 ± 9.0 |
| 90 mM sucrose | 0 | 70 | 13.9 ± 2.2 |
| 90 mM sucrose | 2.6 | 70 | 93.9 ± 7.9 |
| 90 mM maltose | 0 | 0 | 0.0 ± 0.0 |
| 90 mM maltose | 2.6 | 0 | 89.2 ± 8.6 |
| 90 mM maltose | 0 | 30 | 42.2 ± 8.8 |
| 90 mM maltose | 2.6 | 30 | 124.7 ± 18.9 |
| 90 mM maltose | 0 | 70 | 39.8 ± 6.7 |
| 90 mM maltose | 2.6 | 70 | 142.0 ± 27.7 |
| | | Glutamine (mM) | |
| 90 mM sucrose | 0 | 0 | 0.2 ± 0.1 |
| 90 mM sucrose | 2.6 | 0 | 20.8 ± 1.7 |
| 90 mM sucrose | 0 | 10 | 17.9 ± 2.7 |
| 90 mM sucrose | 2.6 | 10 | 26.9 ± 5.9 |
| 90 mM sucrose | 0 | 30 | 36.1 ± 3.5 |
| 90 mM sucrose | 2.6 | 30 | 23.3 ± 0.3 |
| 90 mM maltose | 0 | 0 | 0.0 ± 0.0 |
| 90 mM maltose | 2.6 | 0 | 80.2 ± 10.9 |
| 90 mM maltose | 0 | 10 | 17.0 ± 5.4 |
| 90 mM maltose | 2.6 | 10 | 41.0 ± 18.2 |
| 90 mM maltose | 0 | 30 | 27.4 ± 7.9 |
| 90 mM maltose | 2.6 | 30 | 30.2 ± 4.4 |

EXAMPLE 8

One measure of the quality of embryos produced from cell culture is the conversion frequency, the rate at which embryos form whole plants with roots and leaves. In Table 9 is shown the results of one such experiment in which plantlet formation was compared.

TABLE 9

Conversion frequency of sucrose and maltose reared embryos.

| Initial Carbohydrate Treatment | Embryo Number | Plantlets | Conversion % |
|---|---|---|---|
| 3% sucrose | 35 | 2 | 5.7 |
| 3% maltose | 290 | 26 | 9.0 |

Maltose-treatment causes a 57% higher rate of conversion of embryos to plantlets and hence gives rise to higher quality embryos.

EXAMPLE 9

This frequency of conversion can also be improved by using maltose in the Initial regeneration medium and in the secondary regeneration (conversion) medium, as seen in Table 10.

TABLE 10

Conversion of Somatic Embryos to Plantlets as affected by Initial and Secondary Medium.

| Initial Medium | Secondary Medium | % Conversion |
|---|---|---|
| SH + 25 mM NH$_4^+$ + 3% sucrose | SH + 3% sucrose/2 | 7.5 ± 2.0% |
| SH + 25 mM NH$_4^+$ + 3% maltose | SH + 3% sucrose/2 | 35.6 ± 2.8 |
| SH + 25 mM NH$_4^+$ + 180 mM maltose | SH + 3% sucrose/2 | 37.1 ± 5.0% |
| SH + 25 mM NH$_4^+$ + 300 mM maltose | SH + 3% sucrose/2 | 12.0 ± 2.3% |
| SH + 25 mM NH$_4^+$ + 3% maltose | SH + 3% maltose/2 | 53.2 ± 5.6 |

Thus maltose affects both the initial rearing of embryos and their subsequent maturation and germination.

EXAMPLE 10

As mentioned previously, another measure of embryo quality is the size and morphology of the embryos at a selected time in culture. It has been determined that embryo morphology can be grouped as three distinct types: round, ellipsoid and bottle shaped (see FIG. 1). Bottle shaped embryos are generally larger than the others and appear to have the rudiments of cotyledons and a root radicle. Both round and ellipsoid embryos have been found to dedifferentiate and revert to callus at high frequency Thus, bottle shaped embryos are "converted" more readily than other embryos.

The effect of maltose versus sucrose on embryo size and morphology is shown in Table 11.

TABLE 11

Embryos produced on various carbohydrate sources.

| Treatment | Length (mm) | Width (mm) | % Bottle Shaped |
|---|---|---|---|
| sucrose (3% w/v) | 1.2 ± 0.11 | 0.5 ± 0.03 | 39% |
| maltose (3%) | 2.7 ± 0.23 | 1.04 ± 0.06 | 50% |
| (180 mM) | 3.14 ± 0.19 | 1.17 ± 0.06 | 73% |
| (300 mM) | 2.2 ± 0.15 | 0.99 ± 0.06 | 57% |

Although the foregoing invention has been described in some detail by way of illustration for purposes of clarity of understanding, it will be understood that numerous modifications may be practiced within the spirit and scope of the appended claims.

We claim:

1. In a medium for cultured somatic plant cells, the improvement comprising the inclusion of 7.5 to 300 mM maltose together with at least one amino acid selected from the group consisting of proline, alanine and glutamine in an amount sufficient to increase the number of somatic embryos produced from said plant somatic tissue.

2. A medium as recited in claim 1 further comprising a source of ammonium ions sufficient to provide a final concentration of 2.6 to 100 mM in the medium.

3. A medium as recited in claim 1 or claim 2 wherein the medium further comprises Schenk-Hildebrandt medium.

4. A medium as recited in claim 1 or claim 2 further comprising sucrose in an amount sufficient to stimulate somatic embryogenesis or embryo conversion.

5. In a method of producing embryonic tissue from Leguminosae somatic tissue wherein the somatic tissue is regenerated to form embryonic tissue in a growth medium, the improvement comprising adding 7.5 to 300 mM maltose, together with at least one amino acid selected from the group consisting of proline, alanine and glutamine in an amount sufficient to stimulate somatic embryogenesis or embryo conversion, to said growth medium during the regeneration, induction or conversion phases of somatic embryogenesis.

6. A method as recited in claim 5 further comprising providing a source of ammonium ions sufficient to provide a final concentration of 2.6 to 100 mM in the medium.

7. A method as recited in claim 5 or claim 6 wherein the Leguminosae somatic tissue is alfalfa.

8. A method as recited in claim 5 or claim 6 further comprising providing sucrose in the medium in an amount sufficient to stimulate somatic embryogenesis or embryo conversion.

9. A method as recited in claim 5 or claim 6 wherein the growth medium comprises Schenk-Hildebrandt medium.

* * * * *